(12) United States Patent
Guo et al.

(10) Patent No.: US 7,985,215 B2
(45) Date of Patent: Jul. 26, 2011

(54) DEFLECTABLE CATHETER WITH DISTAL DEFLECTABLE SEGMENT

(75) Inventors: Xiaoping Guo, Eden Prairie, MN (US);
Troy T. Tegg, Elk River, MN (US);
Richard E. Stehr, Stillwater, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 132 days.

(21) Appl. No.: 11/966,550

(22) Filed: Dec. 28, 2007

(65) Prior Publication Data

US 2009/0171348 A1 Jul. 2, 2009

(51) Int. Cl.
*A61M 25/00* (2006.01)
(52) U.S. Cl. .................................................. 604/528
(58) Field of Classification Search .............. 604/19, 604/528, 95.04
See application file for complete search history.

(56) References Cited

U.S. PATENT DOCUMENTS

| 2006/0184106 A1* | 8/2006 | McDaniel et al. | 604/95.04 |
| 2006/0217755 A1* | 9/2006 | Eversull et al. | 606/191 |
| 2006/0282151 A1* | 12/2006 | Weber et al. | 623/1.11 |

* cited by examiner

*Primary Examiner* — Nicholas D Lucchesi
*Assistant Examiner* — Pritesh Patel
(74) *Attorney, Agent, or Firm* — Marsh Fischmann & Breyfogle LLP

(57) ABSTRACT

A guidable, or steerable, or deflectable catheter is provided that includes a proximal portion and a distal portion for insertion into a body cavity. A selectively deflectable segment having an anisotropic bending stiffness for deflection in individual planes is incorporated into the distal portion of the catheter shaft. Upon actuation of pull wires, the distal deflectable segment may be deflected to move/sweep the distal catheter tip through a sweeping plane. The anisotropic bending stiffness of the distal deflectable segment permits in-plane movement of the distal catheter tip in the sweeping plane while resisting any out-of-plane movements. In one arrangement, stiffening elements are selectively disposed within the distal deflectable segment such that the out-of-plane bending stiffness is largely increased and greater than the in-plane bending stiffness for deflection in the sweeping plane. In another arrangement, the cross section of a distal deflectable segment is altered to produce anisotropic area inertias of moment about its centroidal axes, and thus anisotropic bending stiffnesses.

36 Claims, 9 Drawing Sheets

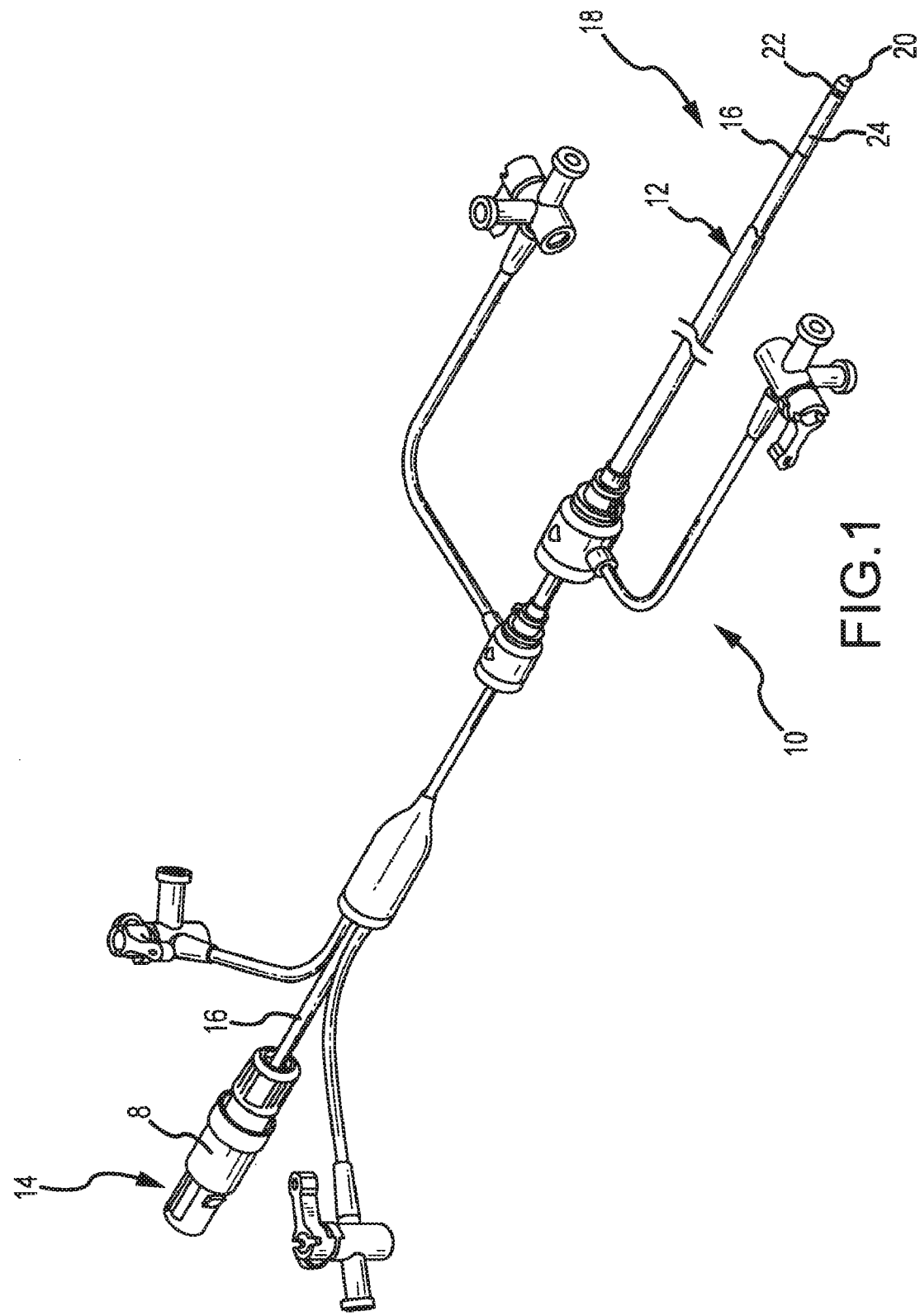

IN-PLANE (xoz) BENDING STIFFNESS     OUT-OF-PLANE BENDING STIFFNESS

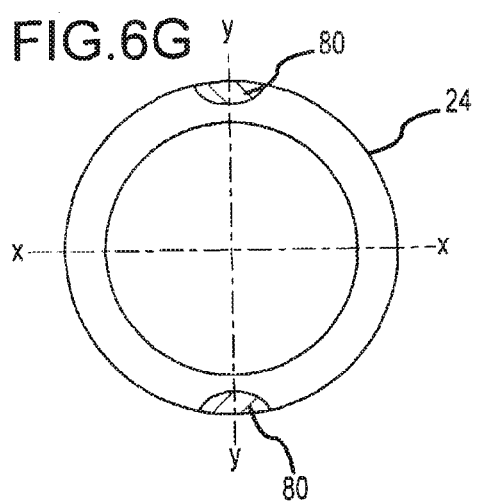
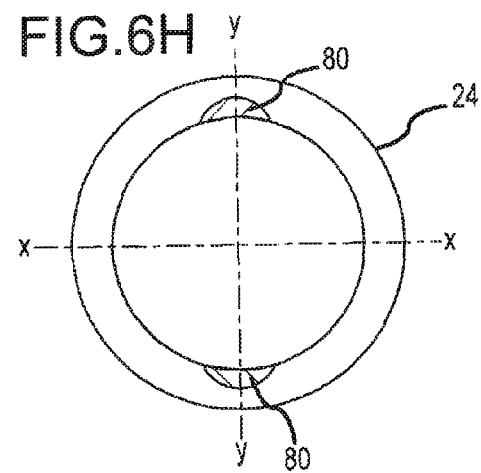
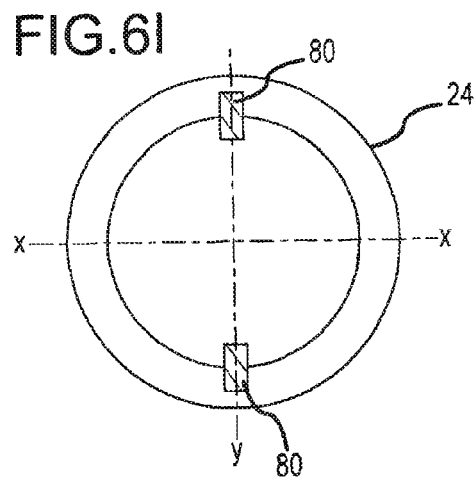
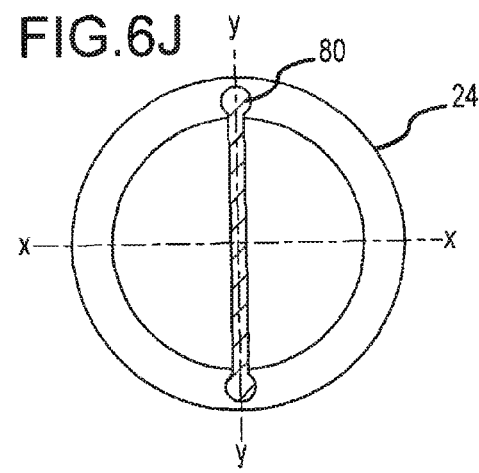

FIG.7A
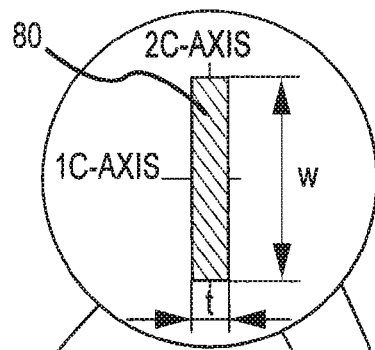
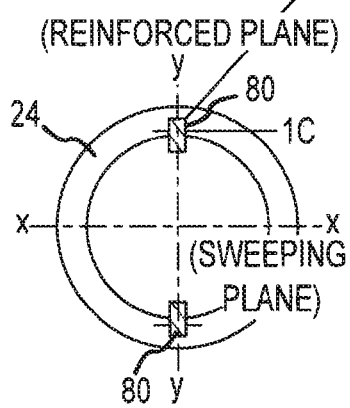
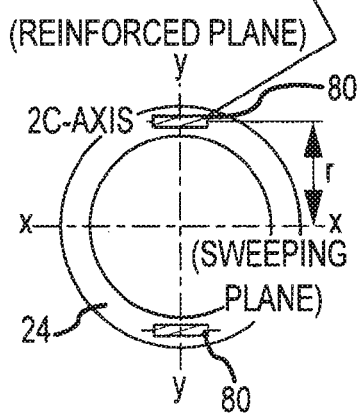
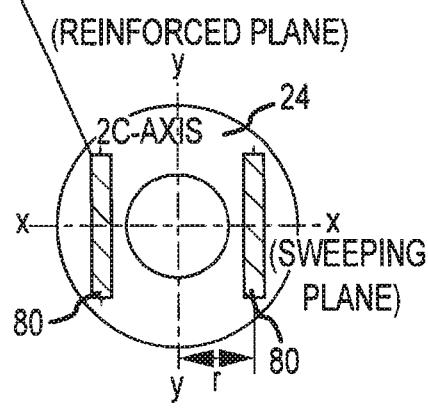
FIG.7B  FIG.7C  FIG.7D

DEFLECTABLE CATHETER WITH DISTAL DEFLECTABLE SEGMENT

BACKGROUND OF THE INVENTION a. Field of the Invention

The invention generally relates to catheters for guided introduction into a body cavity. More specifically, the invention relates to a catheter that includes a distal deflectable segment having an anisotropic deflecting (or bending) stiffness that reduces or eliminates unintended out-of-plane movement of a distal end of the catheter.

b. Background Art

Catheters can be used for medical procedures to examine, diagnose, and treat while positioned at a specific location within the body that is otherwise inaccessible without more invasive procedures. During these procedures a catheter is typically inserted into a vessel near the surface of the body and is guided to a specific location within the body for examination, diagnosis, and treatment. For example, catheters can be used to convey an electrical stimulus to a selected location within the human body, e.g., for tissue ablation, as well as to monitor various forms of electrical activity in the human body, e.g., for electrical mapping. Catheters are also being used increasingly for medical procedures involving the human heart. In such cases, the catheter is typically inserted in an artery or vein in the leg, neck, or arm of the patient and guided, sometimes with the aid of a guide wire or introducer, through the vessels until a distal end of the catheter reaches a desired location in the heart.

In a normal heart, contraction and relaxation of the heart muscle (myocardium) takes place in an organized fashion as electro-chemical signals pass sequentially through the myocardium. Sometimes abnormal rhythms occur in the heart, which are referred to generally as cardiac arrhythmia. The cause of such arrhythmia is generally believed to be the existence of an anomalous conduction pathway or pathways that bypass the normal conduction system. An increasingly common medical procedure for the treatment of certain types of cardiac arrhythmia is catheter ablation. During conventional catheter ablation procedures, an energy source is placed in contact with cardiac tissue (e.g., associated with an anomalous conduction pathway) to create a permanent scar or lesion that is electrically inactive or noncontractile. The lesion partially or completely blocks the stray electrical signals to lessen or eliminate arrhythmia. As will be appreciated, ablation of a specific location within the heart requires the precise placement of the ablation catheter within the heart.

Guidance of a catheter to a specific location in the body can be performed using feel, electrophysiological guidance, computer generated maps/models and/or a combination of the above. In any case, it may be necessary to deflect the distal end of the catheter to facilitate movement of the catheter through a body cavity (e.g., vessel) and/or to position the distal end of the catheter relative to an internal structure of interest. In this regard, guidable catheters and/or introducers typically include a selectively deflectable segment near their distal tip. For instance, an ablation catheter may include a distal end portion (e.g., insertion portion) having an ablation electrode and a soft and flexible distal deflectable segment that is disposed between the electrode and the relatively rigid (e.g., metallic wire-braided) catheter shaft that extends to a proximal actuator. Pull wires extend through the deflectable segment and attach to a pull ring (e.g., positioned between the deflectable segment and the electrode). The pull wires extend through the catheter and are axially connected to a pull mechanism of the proximal actuator. Upon the deflection by manipulating the actuator, the pull wires generate a pull force that imposes a bending moment on the flexible deflectable segment. This leads to the deflection of the distal end of the catheter, which allows the distal end to be routed to and/or positioned relative to desired internal locations.

Several difficulties may be encountered, however, when attempting to precisely locate the distal end of a catheter at an internal location of interest for guidance purposes and/or for performing an internal procedure, such as, for example, ablating tissue.

BRIEF SUMMARY OF THE INVENTION

In order to facilitate deflecting movement of the distal tip of a catheter, it may be desirable to constrain the movement of the catheter tip to a consistent and repeatable plane when actuated by a pull wire. That is, upon pulling a pull wire (e.g., actuation) to deflect the distal tip of the catheter, it may be desirable that the catheter tip deflect within a sweeping plane that is repeatable from actuation to actuation. However, due to the previous construction of distal deflectable segments, the tip of the catheter is often able to move out of the desired sweeping plane. That is, it has been determined that deflecting movement of the distal tip may not be consistent between actuations. Therefore, it is desirable to provide a distal deflectable segment that constrains the movement of the distal tip of the catheter in a predictable and consistent manner. Accordingly, the present invention is directed to a distal deflectable segment that permits its deflecting movement within one plane (i.e. "in-plane" or "sweeping plane"), while resisting unintended movements in other plane (i.e. "out-of-plane").

According to a first aspect, a guidable catheter is provided. The catheter includes a catheter body that has a proximal portion and a distal portion where the distal portion is adapted for insertion into a body cavity (e.g., internal tissue lumen, blood vessel, etc.). A selectively deflectable segment is incorporated into the distal portion of the catheter body. The selectively deflectable segment may be interconnected (e.g., axially) to the proximal portion of the catheter body by one or more pull wires. Upon actuation of such pull wires the distal deflectable segment may be deflected to move/sweep the distal catheter tip within a virtual plane called a sweeping plane. To maintain tip movement in a desired sweeping plane, the deflectable segment has a first bending stiffness for deflection in a first plane and a second bending stiffness for deflection in a second plane where the first bending stiffness and the second bending stiffness are different.

Generally, a bending stiffness for deflection in one plane is significantly larger than a bending stiffness for deflection in other plane. That is, one of the planes may be significantly stiffer than other plane under a deflecting, or flexing or bending deformation mode. Accordingly, the tip movement of the deflectable segment may be substantially isolated to a single, virtual plane, i.e. sweeping plane. In one arrangement, the bending stiffness for deflection in one of the planes can be enhanced to form a reinforced plane. The bending stiffness for deflection in the reinforced plane is at least 5% greater than the bending stiffness for deflection in the other plane. In a further arrangement, the stiffness may be at least twice the stiffness for deflection in the other plane. In a yet further arrangement, the stiffness may be at least 10 times greater than the stiffness for deflection in the other plane.

Generally, the plane, for deflection in which a deflectable segment has the greater bending stiffness, may define a reinforced plane of the segment, while the plane, for deflection in which the segment has the lower bending stiffness may define a virtual, sweeping plane. The sweeping plane is typically perpendicular to the reinforced plane, and both planes pass through a reference, longitudinal axis (e.g., central axis) of the deflectable segment along its length. In one arrangement, the guidable catheter may also include a first pull wire that extends through at least a portion of the length of the deflectable segment. In a particular arrangement, the pull wire and/or its endpoints or end-lines anchoring onto the deflectable segment, may be substantially disposed within the sweeping plane. However, it will be appreciated that due to the high bending stiffness for deflection in the reinforced plane, minor misplacement of the pull wire(s) away from the sweeping plane may not result in out-of-plane movement of the distal end of the catheter body upon deflection of the deflectable segment.

In one reinforced plane arrangement, the selectively deflectable segment further includes a stiffening element that is disposed along at least a portion of the length of the deflectable segment. The stiffening element may extend over the entirety of the length of the deflectable segment and/or multiple stiffening elements may be disposed in, for example, series and/or parallel. In one arrangement, stiffening elements have a Young's modulus that is greater than the Young's modulus of the flexible material (e.g., polymeric material) forming the deflectable segment. In such an arrangement, stiffening elements may be formed of, for example, relatively rigid polymeric material and/or metallic material. In any arrangement, the cross section of a stiffening element may have an area moment of inertia about a first centroidal axis that is greater than an area moment of inertia about a second centroidal axis. In this regard, the stiffening element may permit bending or deflection in a plane in parallel with the first centroidal axis, while significantly restricting bending in another plane. Accordingly, such a stiffening element may be disposed in the vicinity of a reinforced plane of a distal deflectable segment to prevent out-of-plane movement while permitting in-plane movement (e.g., sweeping plane movement).

In one arrangement, in a non-deflected state, the deflectable segment has a substantially circular cross-section and an internal lumen. In a further arrangement, the internal lumen shares a cross-sectional shape with the outside surface of the deflectable segment. In such an arrangement, the deflectable segment may be a tubular segment having a substantially constant sidewall thickness. One or more stiffening elements may be disposed within the sidewall. In a further arrangement, an electrode may be connected to the distal end of the catheter body (e.g., distally to the selectively deflectable segment). Such an electrode may be utilized for mapping purposes and/or tissue ablation.

In another aspect, a guidable catheter is provided having a distal deflectable segment. In a non-deflected state, a length of the deflecting statement defines a reference longitudinal axis between its proximal and distal ends. At least one stiffening element extends over at least a portion of the length of the deflectable segment between its proximal and distal ends. The catheter further includes at least one pull wire that extends through the deflectable segment for selectively moving the deflectable segment from a non-deflected state to a deflected state.

In one arrangement, the distal deflectable segment is formed of a first material (i.e., body material), and the stiffening element is formed of a second material. In such an arrangement, the second material may have a Young's modulus that is greater than the Young's modulus of the first material for the distal deflectable segment. In one arrangement, the first and second materials may be formed of polymeric materials. For instance, the first material may be a flexible thermoplastic elastomer (TPE) material, and the second material may be a relatively rigid polymeric material having a Young's modulus that is greater than the TPE material. Where two polymeric materials are utilized, the first and second materials may be co-extruded to form the distal deflectable segment. In a further arrangement, the stiffening element may be a preformed polymeric component and/or metallic component made of the second material. Accordingly, the first material of the distal deflectable segment may be melt extruded over and/or laminated to the performed stiffening element.

In another aspect, a guidable catheter is provided having a distal deflectable segment formed of a first material and at least one stiffening material formed of a second material. In a non-deflected state, the deflectable segment is substantially tubular, and the length of the deflectable segment defines a reference longitudinal axis. The stiffening element is incorporated into a sidewall of the deflectable segment and extends over at least a portion of the length of the deflectable segment. In such an arrangement, the distal deflectable segment may define an internal lumen that may be substantially free of intrusion by the stiffening element. That is, in one arrangement, the stiffening element may be fully encapsulated within the sidewall. This may enhance or maximize the size of the lumen for fluid passage and/or passage of devices through the lumen.

According to another aspect, a guidable catheter is provided having a distal deflectable segment that, in a non-deflected state, is substantially tubular and defines a reference longitudinal axis along its length. At least one stiffening element extends over at least a portion of the length of the deflectable segment. The stiffening element has a cross section with an area moment of inertia $I_{1c}$ about its first centroidal axis being at least two to fifty times an area moment of inertia $I_{2c}$ about a second centroidal axis. The stiffening element may be disposed in the vicinity of and/or in alignment with a desired reinforcing plane of the distal deflectable segment, or preferably, the second centroidal axis is in alignment and/or parallel with that plane. What is important is that the stiffening element resists bending or deflecting in the reinforced plane, while permitting bending or deflection in other plane.

According to another aspect, a guidable catheter is provided having a distal deflectable segment that, in a non-deflected state, is substantially tubular and defines a reference longitudinal axis along its length. At least one stiffening element extends over at least a portion of the length of the deflectable segment. The stiffening element has a cross section with an identical area moment of inertia about its two centroidal axes. The stiffening element may be disposed in the vicinity of and/or in alignment with a desired reinforced plane of the distal deflectable segment. What is important is that the stiffening element resists bending or deflecting in the reinforced plane, while permitting bending or deflection in another plane.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 1 is an exemplary catheter system including an introducer and an ablation catheter.

FIG. 3B illustrates internal components of the distal deflectable segment of FIG. 3a.

FIGS. 6A-6J illustrates various embodiments of distal deflectable segments incorporating one or more stiffening elements aligning with a reinforced plane.

FIG. 7A-7D illustrates a further embodiment of an anisotropic stiffening element and a distal deflectable segment incorporating one or more of that element.

DETAILED DESCRIPTION OF THE INVENTION

Exemplary embodiments of a catheter system and methods of using the system to access internal areas of interest are depicted in the figures. As described further below, use of a catheter having a distal deflectable segment having anisotropic bending properties allows for improved catheter guidance and/or improved control for tissue access/contact.

Figure 2A:
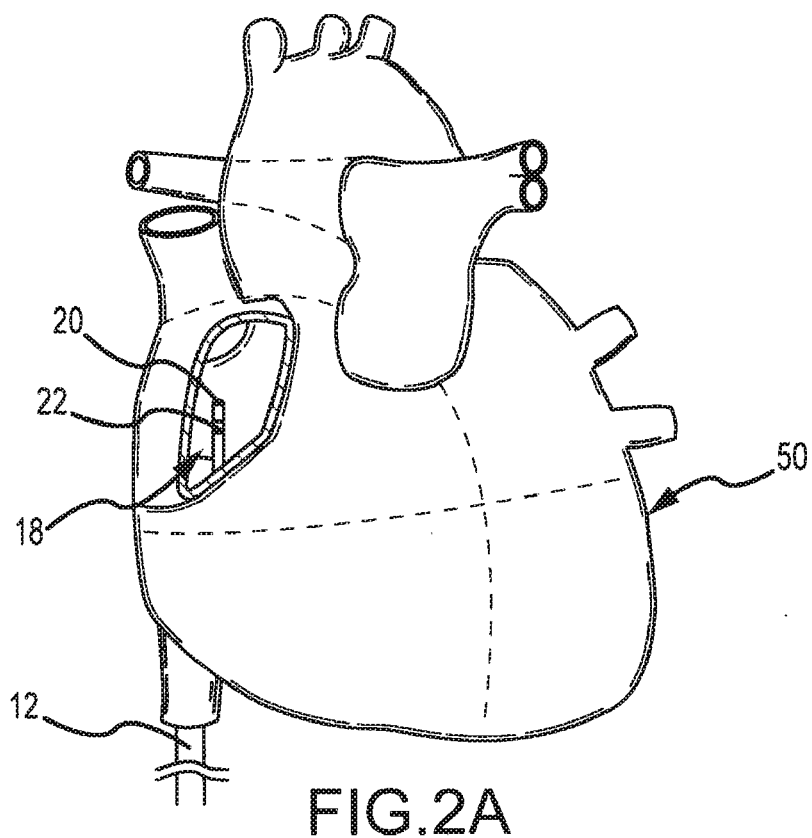
FIG. 2A illustrates an electrode catheter disposed in a heart with a distal deflectable segment in a non-deflected state.

FIG. 1 illustrates an exemplary electrode catheter system that may be utilized to access, map and/or perform medical procedures on internal tissue of interest. The catheter system 10 may include a guiding introducer having a sheath 12, which may be inserted into a patient. The sheath 12 may provide a lumen for the introduction of a catheter 18 which may be disposed beyond the distal insertion end of the sheath 12. In the particular configuration of FIG. 1, the sheath 12 is configured to receive and guide the catheter 18 to an internal location in the heart once the sheath is pre-positioned in an appropriate location. During an exemplary cardiac procedure, a user (e.g., the patient's physician or a technician) inserts the sheath 12 of the introducer into one of the patient's blood vessels (e.g., through the leg or neck). The user, typically guided by an imaging device (e.g., fluoroscopy, ICE, electro-anatomical mapping, etc.) moves the sheath 12 into the patient's heart 50. See FIG. 2A. When the sheath 12 of the guiding introducer is positioned in a desired location within the heart 50 of the patient, the electrode catheter 18 may be extended through a lumen of the sheath 12 such that the electrode catheter 18 may be guided to a desired location within the heart to perform, for example tissue mapping and/or tissue ablation. However, the catheter 18 may be used alone or with other guiding and introducing type devices depending on the particular procedure being performed.

As shown in FIG. 1, the catheter includes a tubular body or shaft 16 extending from a proximal handle 14, through the sheath 12 and extending out of the distal end of the sheath 12. As used herein and commonly used in the art, the term "distal" is used generally to refer to components of the system, such as a tip electrode 20, located toward the insertion end of the of the catheter 18 (i.e., toward the heart or other target tissue when the catheter is in use). In contrast, the term "proximal" is used generally to refer to components or portions of the system that are located or generally orientated toward the non-insertion end of the catheter (i.e., away from or opposite the heart or other target tissue when the catheter is in use).

The proximal handle 14 includes a sliding actuator 8 that is interconnected via one or more pull wires to a distal deflectable segment 24 that is incorporated into the distal portion of the catheter 18. As shown in FIG. 1, the distal tip of the exemplary catheter includes an ablation tip/electrode 20. Located proximally behind the electrode 20 is a pull ring 22 and the distal deflectable segment 24. The proximal end of the distal deflectable segment 24 is connected to the distal end of the catheter shaft 16. Generally, the catheter shaft 16 is more rigid that the generally soft and flexible distal deflectable segment 24. For instance, the catheter shaft 16 may be formed of a flexible resilient material covered by a wire-braiding that may extend to the proximal handle 14.

In one exemplary embodiment, the sheath 12 and shaft 16 are fabricated with a flexible resilient material. The sheath and the components of the catheter are preferably fabricated of materials suitable for use in humans, such as biocompatible polymers. Suitable polymers include those well known in the art, such as numerous thermoplastics including, but not limited to, Fluoropolymers, polyolefins, polyesters, polyamides, polycarbonate, polyurethanes, polyimides, polysulfones, polyketons, liquid crystal polymers and the like. Various thermoplastic elastomer (TPE) materials can be also selected, including, but not limited to thermoplastic polyurethanes, polyamide-based TPE's, polyester-based TPE's, thermoplastic polyolefins, styrenic TPE's and the like.

Figure 2B:
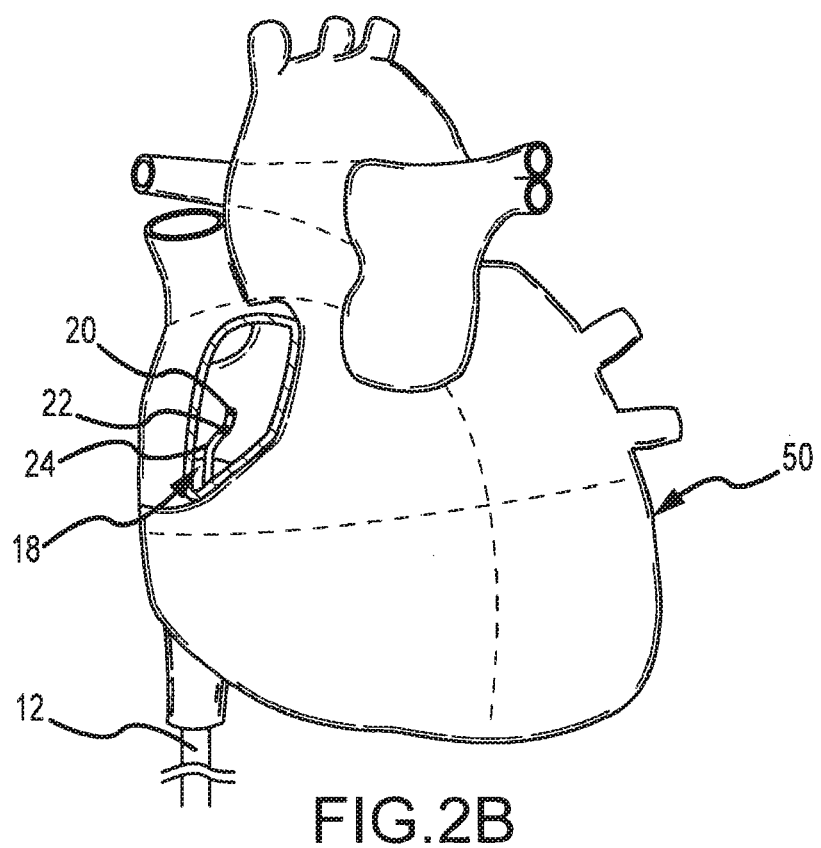
FIG. 2B illustrates an electrode catheter disposed in a heart with a distal deflectable segment in a deflected state
Figure 3A:
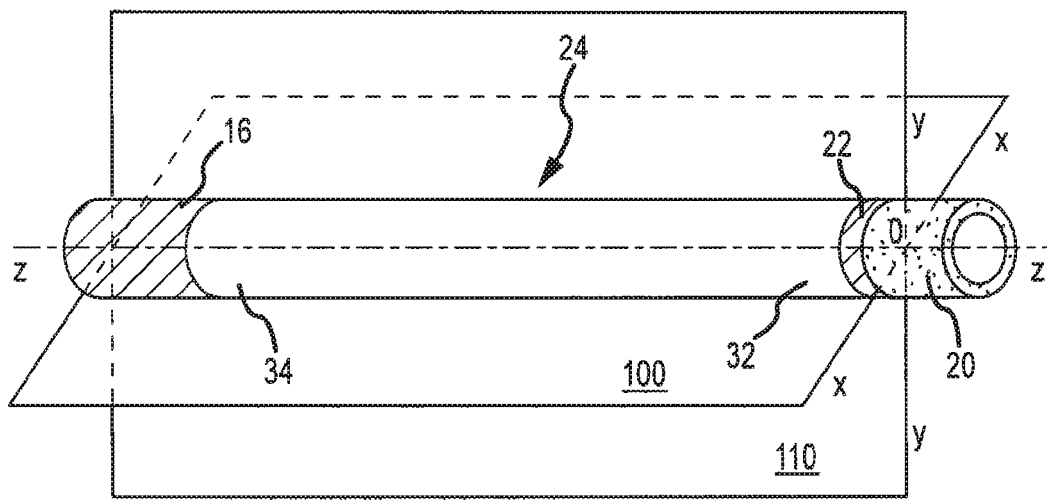
FIG. 3A illustrates a distal deflectable segment in a non-deflected state.
Figure 3B:
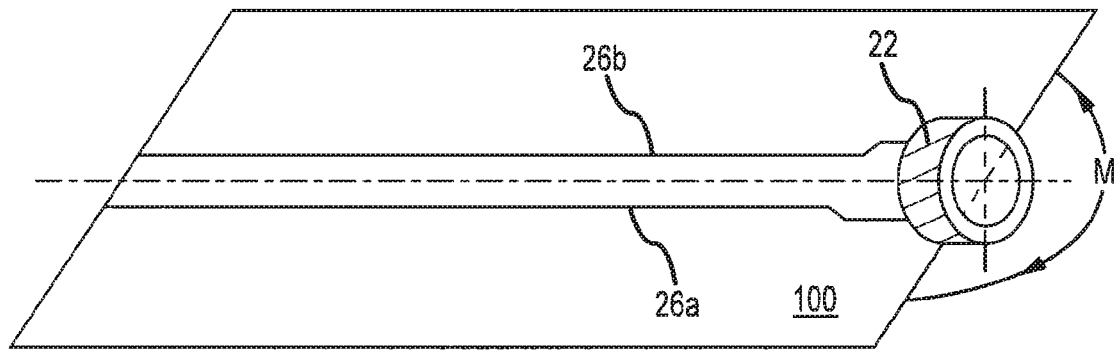
Figure 3C:
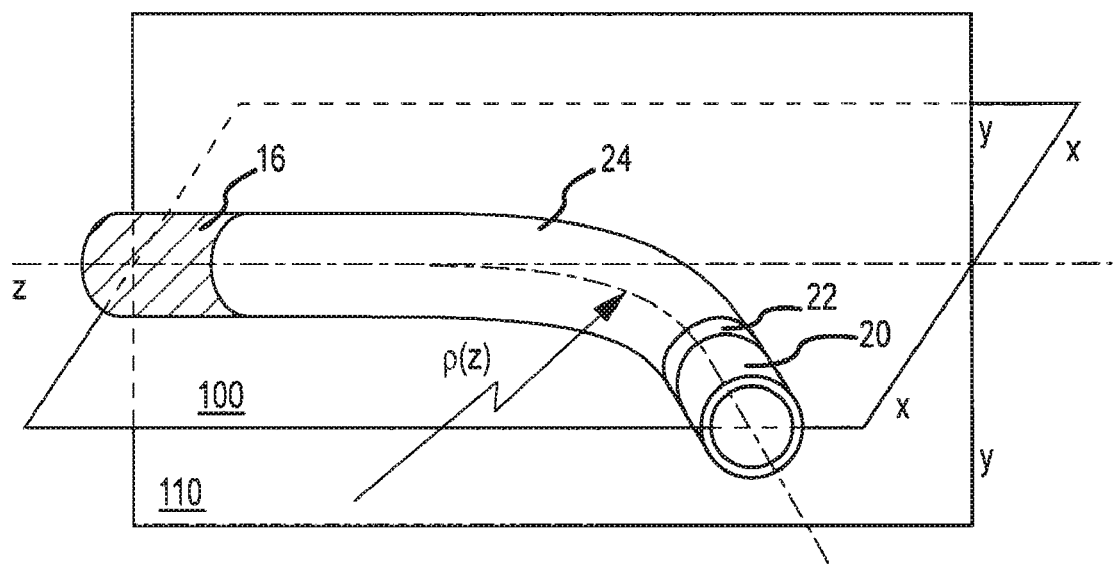
FIG. 3C illustrates the distal deflectable segment of FIG. 3a in a deflected state.

FIGS. 3A-3C variously illustrate the distal deflectable segment. As shown in FIG. 3A, in a non-deflected state, the distal deflectable segment 24 extends, as a substantially tubular structure, between the distal end of the catheter shaft 16 and the tip electrode 20. In order to deflect the deflectable segment 24, pull wires 26A, 26B (generally 26 unless individually referenced) extend from the sliding actuator 8, through the shaft 16 and deflectable segment 24 and attach to a pull ring 22. This is illustrated in FIG. 3B, where the deflectable segment, shaft and electrode are removed for purposes of illustration. Upon the deflection by manipulating the actuator 8, the pull wires 26 generate eccentric pull force on the pull ring 22, which imposes the bending moment M on the flexible distal deflectable segment 24. As illustrated in FIG. 3C, this deflects of the distal end of the catheter and thereby allows for disposing the distal tip of the catheter relative to internal areas of interest. See also e.g., FIG. 2B.

More specifically, as illustrated in FIG. 3C the distal tip (e.g., tip electrode 20) of the catheter 18 is caused to move within a bending or sweeping plane 100. As may be appreciated, for precise placement and guidance of the distal tip of the catheter to an internal location of interest, it may be desirable that the deflection of the distal tip be constrained only within the sweeping plane 100. Such constraint to the desired sweeping plane may provide consistent and predictable displacement between deflections of the catheter. However, the flexible distal deflectable segments currently used for most deflectable catheters are simply hollow tubes typically made of a single polymer material that is typically soft and flexible. Such deflectable segments have not resulted in constrained (i.e., in-plane) deflection or consistency between deflections. That is, previous deflectable segments have permitted some out-of-plane movement.

In this regard, the sweeping planes of previous distal deflectable segments have depended on the direction of the bending moment (M) imposed on the distal deflectable segment and the isotropic bending stiffness of a generally hollow polymeric tube. As illustrated in FIG. 3B, pull wires 26A, 26B may be disposed in a common plane with the sweeping plane. By pulling axially on one of the wires 26 (e.g., using the actuator 8), a bending moment M may be applied to the distal deflectable segment 24 which causes the distal tip (e.g., electrode 20) of the catheter to move in plane (i.e., the sweeping plane 100) that includes the pull wires 26.

To ensure the sweeping planarity and consistency of deflectable segment 24, the pull wire-generated pull force or bending moment M must be in near perfect alignment with the designated sweeping plane 100 as shown in FIG. 3B. This is a challenge for part assembly during manufacturing as misalignment between the pull wires 26, pull ring 22 and the desired sweeping plane 100 is almost unavoidable. Such misalignment typically results in the distal tip of the catheter 18 moving at least partially outside of the sweeping plane 100. That is, misalignment results in non-planarity issues for deflectable catheters. Further, during use, small disturbance in the directions of the pull force or bending moment and/or minor internal inconsistencies of the hollow polymeric tube will allow the distal deflectable segment to deflect outside of the sweeping plane. This leads to twisting or torsion of the distal deflectable segment and the movement of the distal end in an unpredictable way. The result is that it may be difficult to guide the distal tip of the catheter or an introducer to a desired internal location of interest in a highly controlled manner.

To overcome these problems, the distal deflectable segment 24 of the present invention utilizes an anisotropic bending stiffness such that deflection of the segment 24 may be more effectively isolated to a desired plane (e.g., the sweeping plane). As will be discussed herein, embodiments of such an anisotropic deflectable segment may be produced by altering the physical cross-sectional dimensions of the segment and/or by incorporating one or more stiffening elements into the segment. In the latter regard, it will be appreciated that based on the combinations of at least two different materials (e.g., forming the stiffening element and deflectable segment) having significantly different material stiffness (e.g., Young's moduli), a resulting distal deflectable segment 24 may possess anisotropic bending stiffness for deflection in different planes. Stated otherwise, the incorporation of a stiffening element into the deflectable segment may only allow deflection or catheter tip sweeping within a designated plane and structurally prevent any deflection out of the designated plane (i.e., out-of-plane movement).

Referring again to FIG. 3A, coordinate system is set forth for purposes of discussion and not by way of limitation. Specifically, in a non-deflected state, the distal deflectable segment 24 is a generally tubular structure and its long axis defines a reference longitudinal axis (e.g., z axis) between its distal end 32 and its proximal end 34. In this embodiment, while the segment is non-deflected, the sweeping plane 100 defines the x axis as illustrated in subsequent Figures. The plane 110 that is perpendicular to the sweeping plane 100, and which extends through the reference longitudinal axis, defines the y axis in the subsequent Figures. In a non-deflected state, the plane 110 that incorporates the reference longitudinal axis and is perpendicular to the sweeping plane defines a reinforced plane 110. In the following Figures, it will be appreciated that the cross sections of the distal deflectable segment 24 reside in the plane (i.e., xy plane) that is perpendicular to the sweeping plane 100 and the reinforced plane 110 as well as the longitudinal axis of the deflectable segment (i.e. z axis).

Figure 4:
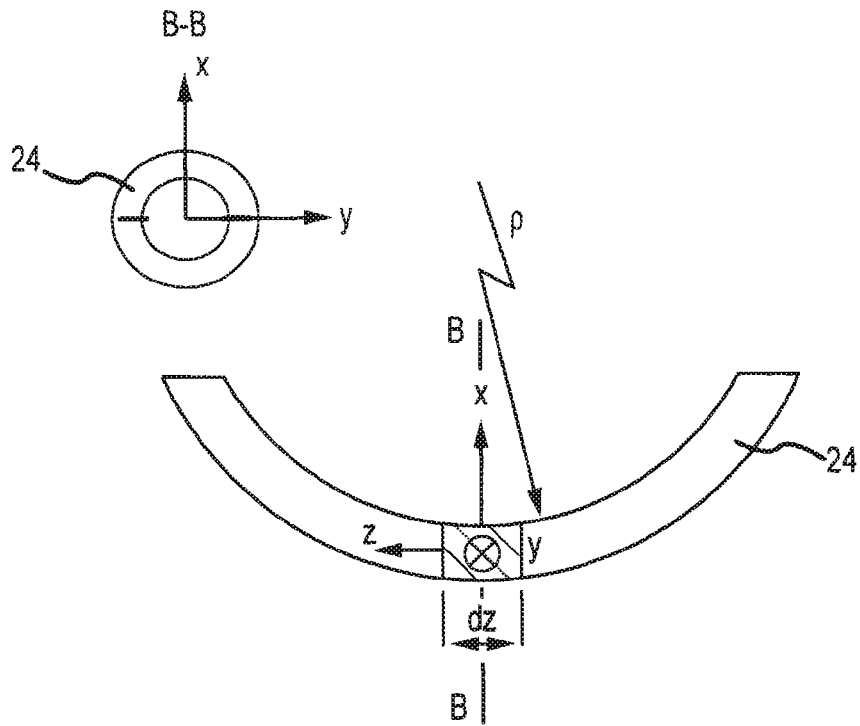
FIG. 4 illustrates local deflection of a distal deflectable segment in the sweeping plane (i.e. xz plane).

FIG. 4 shows the deflection of the distal deflectable segment 24 under a pure bending moment imposed by the pull ring 22 and the localized infinitesimal portion of the distal deflectable segment 24, dz, at the axial position of z (i.e. located along the reference longitudinal z-axis). From beam theory, the bending stiffness, S, for deflection in a plane is related to the localized deflection curvature radius, ρ, via the following equation:

$$\frac{1}{\rho} = \frac{M}{S}; \quad S = \int E \, dI \qquad \text{Eq. (1)}$$

where M is the bending moment in or along the plane; E is the material stiffness (or Young's modulus) and I is the area moment of inertia (i.e. second moment of area) relative to the neutral bending axis of the cross section of the deflectable segment, which is perpendicular to the plane. It will be appreciated that for a given bending moment, low bending stiffness for deflection in the plane will introduce large deflection (i.e. smaller curvature radius). Thus, bending stiffness for deflection in a plane may be considered a direct measure for the deflection occurring in the plane. In this sense, low bending stiffness for deflection in the sweeping plane 100 is preferred to promote in-plane deflection, while high bending stiffness for deflection in reinforced plane 110 (at non-deflecting state) is required to prevent out-of-plane movement of the distal deflectable segment. For in-plane deflection of the deflectable segment 24 in sweeping plane 100, local interception line of the reinforced plane 110 with the cross section of the segment 24, namely y-axis, is the local neutral bending axis of the cross section of the segment 24. For out-of-plane deflection of the deflectable segment 24, local intercept line of sweeping plane 100 with the cross section of the segment 24, namely x-axis, is the local neutral bending axis of the cross section of the segment 24.

To minimize or prevent the deflection deviations in planes other than the designated sweeping plane 100, the bending stiffness in these other planes may be increased, while still maintaining low bending stiffness for in-plane deflection in the sweeping plane. This leads to the anisotropic bending stiffness for a given cross section of the distal deflectable segment 24. For this purpose, referring to FIG. 5, the in-plane and out-of-plane bending stiffness can be defined as:

$$S^{in\text{-}plane} = \int E \, dI = \int E(x) \cdot x^2 \, dA \qquad \text{Eq. (2)}$$

$$S^{out\text{-}of\text{-}plane} = \int E \, dI = \int E(y) \cdot y^2 \, dA \qquad \text{Eq. (3)}$$

wherein for promoting in-plane deflection in sweeping plane 100 and preventing any deflections in other plane, it must meet that:

$$S^{in\text{-}plane} \ll S^{out\text{-}of\text{-}plane}. \qquad \text{Eq. (4)}$$

Figure 5:
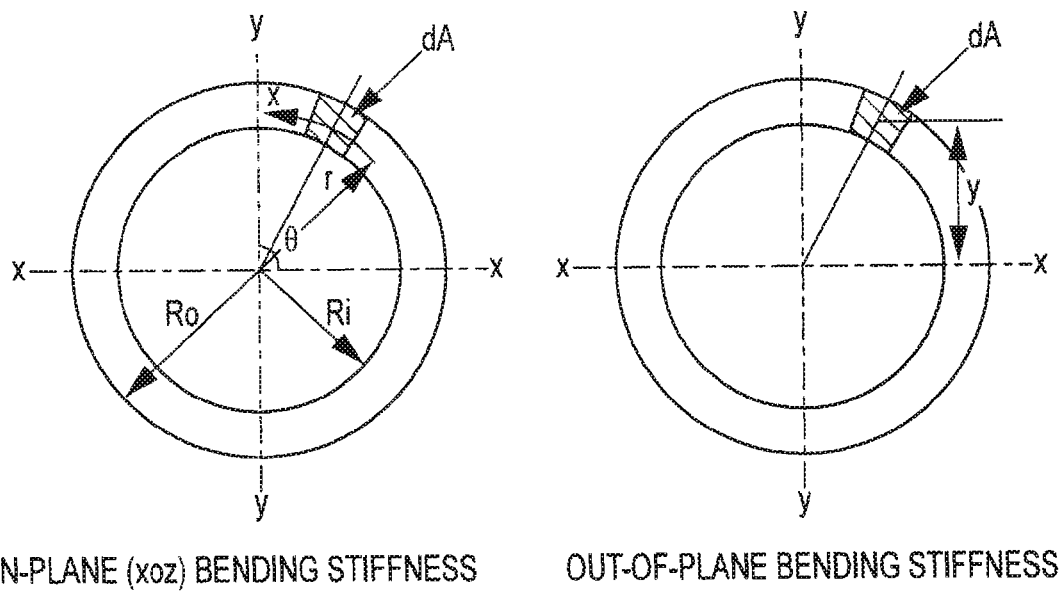
FIG. 5 illustrates in-plane and out-of-plane bending stiffness in the cross-sectional area of a distal deflectable segment.

It will be appreciated that a tubular deflectable segment formed of an isotropic material will have the same bending stiffness for the in-plane deflection (i.e., the deflection about the neutral in-plane bending axis, namely y-axis) and the out-of-plane deflection (i.e., the deflection about the neutral out-of-plane bending axis, namely x-axis). Accordingly, to permit the in-plane deflection in the sweeping plane 100 (e.g. xz-plane) about a neutral in-plane bending axis (e.g. y-axis) while preventing the out-of-plane deflection in the reinforced plane 110 (e.g. yz-plane) about the neutral out-of-plane bending axis (e.g. x-axis), it is desirable to increase the out-of-plane bending stiffness. As illustrated in FIG. 5, this entails that for designing the cross section of a distal deflectable segment 24, the area moment of inertia about its neutral out-of-plane bending axis (i.e. x-axis) shall be increased, without significantly changing the other area of moment of inertia about the neutral in-plane bending axis (i.e. y axis).

In a first arrangement, an out-of-plane bending stiffness is increased by including a stiffening element that is incorporated into the cross-section of the deflectable segment at a location that increases the overall moment of inertia about the neutral out-of-plane bending axis (i.e. x-axis) without significantly changing the area moment of inertia about the neutral in-plane bending axis (i.e. y-axis), about which the deflectable segment will be deflected in the sweeping plane 100 (i.e. xz-plane) as a whole entity. Broadly stated, inclusion of one or more stiffening elements having a material stiffness (i.e., Young's modulus) that is greater than the flexible material used to form the distal deflectable segment 24, may allow an out-of-plane bending stiffness (i.e. $S^{out\text{-}of\text{-}plane}$) about the neutral out-of-plane axis (i.e. x-axis), per Eq. 3, to be significantly increased, while minimally changing the in-plane bending stiffness (i.e. $S^{in\text{-}plane}$) about the neutral in-plane bending axis (i.e. y-axis), per Eq. (2). Further, it will be appreciated that by increasing the spacing of a stiffening element from one axis (e.g., x axis) that the stiffeners may significantly increase the overall out-of-plane bending stiffness of the distal deflectable segment, per Eq. (3).

That is, by using stiffening materials having different material stiffness than the deflectable segment and proper placement of such stiffeners, various designs for the cross section of the distal deflectable segment can provide very low in-plane bending stiffness ($S^{in\text{-}plane}$) but very high out-of-plane bending stiffness ($S^{out\text{-}of\text{-}plane}$). This will allow deflection within the designated sweeping plane while largely limiting deflection out of the sweeping plane.

FIGS. 6A-6J show a series of designs where stiffening elements 80 are incorporated into sidewall of the distal deflectable segment 24. In all theses designs, shaded areas designate the placement of the rigid materials or stiffening elements 80 having a Young's modulus that is greater than the Young's modulus of the surrounding material of the deflectable segment 24. As shown, the cross-sectional shape of the stiffening elements 80 may be varied. Further, the stiffening elements 80 may, in various embodiments, be entirely encased within the sidewall of the deflectable segment. This may minimize or eliminate intrusion into a lumen defined by the segment 24.

These stiffening elements 80 can be metals or metallic alloys commonly used for reinforcing catheter shafts, including steels, stainless steels, NiTi alloys, tungsten, and others. Also, those stiffening materials can be engineering polymers such as polycarbonates, nylons, polyesters, polyurethanes, nylon-based copolymers, polystyrenes, poly(methyl methacrylate), polysulfones, liquid crystalline polymers, etc. The un-shaded areas in FIGS. 6A-6J (i.e., the sidewall of the deflectable segment 24) have generally smooth, cylindrical outside surfaces extruded from a soft and flexible polymer material, which is commonly used to make current distal deflectable segment. These soft materials may include, without limitations, thermoplastic elastomers (TPE) of all kinds such as polyamide-based TPE (Pebax®, Vestamid® E and the like), polyester-based TPE's (Hytrel® and the like), styrenic TPE (Kraton®, Versaflex®, SIBStar®), and the like), functionalized olefinic TPE (Engage® and the like), ionic TPE's (Surlyn® and the like), thermoplastic polyurethanes (Pellethane®, Estane®, and the like), silicone-urethane TPE (Elaston®, PurSil®, CarboSil®, and the like) and etc. Elastomers or rubbers can be also used, including silicone rubbers and other synthetic rubbers such as polybutadiene, polyisoprene, and the like. When polymeric stiffening elements are used, they will typically have a Young's modulus that is significantly larger than the flexible polymeric material used to form the deflectable segment. The designs shown in FIGS. 6A-6J can be made using conventional melt co-extrusion, melt over-extrusion, extrusion-curing and heat lamination (or reflow) manufacturing processes, dependent of the rigid and flexible material pairs as well as the cross-sectional geometry used for the design of the distal deflectable segment 24.

For the designs shown in FIGS. 6A-6J, the stiffening elements 80 are placed where x~0 in the cross section of the distal deflectable segment 24. That is, the stiffening elements are placed near a neutral in-plane bending axis (i.e. y-axis). Therefore, the stiffening elements 80 have minimal contribution to the in-plane bending stiffness about the neutral in-plane bending axis (i.e. y-axis), per Eq. (2). However, due to high Young's modulus of the stiffening material 80 and its placement along the reinforced plane 110 (i.e. yz-plane) and near the outside diameter of the cross section of the distal deflectable segment 24, the stiffening element 80 significantly increases the out-of-plane bending stiffness about the neutral out-of-plane bending axis (i.e. x-axis), per Eq. (3). Therefore, this combination of a stiffening element in the cross section of the distal deflectable segment 24 leads to high anisotropic bending stiffness for the distal deflectable segment 24 with the out-of-plane bending stiffness being significantly higher than the in-plane bending stiffness. As will be appreciated, deflectable catheters with highly anisotropic bending stiffness in their distal deflectable segments will typically exhibit improved deflecting planarity and consistency and become much less influenced by disturbance of out-of-plane bending moments generated by the pull wires and pull ring. That is, even if the pull wires 26 and their anchoring points on the pull ring 22 are misaligned with the sweeping plane 100, the out-of-plane bending stiffness for deflection in the reinforced plane 110 or about the neutral out-of-plane bending axis (i.e. x-axis) will minimize or prevent the distal tip of the catheter from moving outside of the sweeping plane 100. In this regard, distal deflectable segment 24 allows for improved controllability of the distal catheter deflection and/or improved placement of the catheter relative to internal tissue areas of interest.

While the above exemplary embodiments illustrated in FIG. 6A-6J utilize one or two stiffening elements 80 disposed along, and in the vicinity of, the reinforced plane 110 as well as in symmetry with the desired sweeping plane 100, it will be appreciated that alternative placements of stiffening elements 80 in the deflectable segment 24 may be also effective for promoting in-plane deflection and preventing out-of-plane deflection. Further, stiffening elements may have different shapes and their cross sections may have the same or different area moments of inertia about their neutral centroidal axes. In addition to varying size, shape and/or location of the stiffening elements in the segment 24, it will be appreciated that the stiffening elements may extend over the entirety or only a portion of the length of the distal deflectable segment 24. This may allow for tailoring the deflected shape of the distal deflectable segment.

FIG. 7A illustrates a typical anisotropic stiffening segment 80 whose cross section has large difference in the area moments of inertia about its two centroidal axes, namely 1c and 2c, due to its ribbon-like rectangular shape. The first area moment of inertia about the first centroidal 1c-axis is:

$$I_{1c} = \frac{tw^3}{12} \qquad \text{Eq. (5)}$$

while the area moment inertia about the second centroidal 2c-axis is:

$$I_{2c} = \frac{wt^3}{12} \quad \text{Eq. (6)}$$

wherein the ribbon width, w, is significantly larger than the ribbon thickness, t, in the cross section of the segment 80. It is appreciated from Eq. (5) and Eq. (6) that the area moment of inertia 11, (i.e., geometrical resistance to bending) about the first centroidal axis (i.e. 1c-axis) of the ribbon-like stiffener 80 is much greater than the area moment of inertia $I_{2c}$ about the second centroidal axis (i.e. 2c-axis) because w>>t. That is, the shape of the stiffening element 80 provides an anisotropic bending stiffness, aid may be advantageously used to increase the out-of-plane bending stiffness in a more effective way. Therefore, by incorporating one or more stiffening elements 80 into the distal deflectable segment in such a way that the first centroidal axis (i.e. 1c-axis) of the stiffener 80 is in parallel with the sweeping plane 100 and that the second centroidal axis is aligned with the reinforced plane 110, the bending stiffness of the deflectable segment 24 for deflection in the reinforced plane could be maximized. This embodiment is shown in FIG. 7B, and also in FIG. 6D and 6I.

Another embodiment for disposing an anisotropic stiffening elements 80, as shown in FIG. 7A, in the deflectable segment 24 is further illustrated in FIG. 7C, where the first centroidal axes of the stiffening element is aligned with the reinforced plane 110 of the deflectable segment while the second centroidal axis is in parallel with the sweeping plane 100. It will be appreciated that under certain conditions, such placement of the stiffening elements may still largely enhance the out-of-plane bending stiffness, namely $S^{out-of-plane}$, while the in-plane bending stiffness, namely $S^{in-plane}$, is kept relatively small. For instance, where the stiffening elements 80 are formed of metallic material, which has significantly higher Young's modulus (i.e. $E_s$) than the flexible polymeric materials forming the deflectable segment 24 (i.e. E). In general, Young's modulus of a metallic element 80 is hundreds of, even thousands of times the Young's modulus of a soft, flexible polymeric material forming the body of the segment 24. Therefore, it can be further appreciated that the contribution of the elements 80 to the in-plane bending stiffness, $\Delta S^{in-plane}$, and the contribution to the out-of-plane bending stiffness, $\Delta S^{out-of-plane}$, are equivalent to the respective bending stiffness of the deflectable segment 24. That is, $$S^{in-plane} \approx \Delta S^{in-plane} \text{ and } S^{out-of-plane} \approx \Delta S^{out-of-plane} \quad \text{Eq. (7)}$$

Using transfer formula for area moment of inertia, it can be further appreciated that $$S^{out-of-plane} \cong 2E_s I_x \quad \text{Eq. (8)}$$
$$= 2E_s(twr^2 + I_{2c})$$
$$= 2E_s\left(tw \cdot r^2 + \frac{1}{12}wt^3\right)$$

$$S^{in-plane} \cong 2E_s I_y \quad \text{Eq. (9)}$$
$$= 2E_s I_{1c}$$
$$= \frac{1}{6}E_s tw^3$$

From Eq. (8) and (9), it will be appreciated that if the distance of the element 80 from the sweeping plane 100 is comparable to the width of the ribbon-like, rectangular stiffening element 80, e.g. r~w. the out-of-plane bending stiffness can be at least twelve times the in-plane bending stiffness.

Yet another embodiment for disposing an anisotropic stiffening elements 80, shown in FIG. 7A, in the deflectable segment 24 is illustrated in FIG. 7D, where the first centroidal axes (i.e. 1c-axes) of the ribbon-like stiffening element 80 is aligned with the sweeping plane 100 at a distance (namely r) from the reinforced plane 110. Similar to the above discussion, it can be appreciated that the in-plane bending stiffness and the out-of-plane bending stiffness of a deflectable segment 24, which is incorporated with metallic elements 80, can be approximated as follows, $$S^{out-of-plane} \cong 2E_s I_x \quad \text{Eq. (10)}$$
$$= 2E_s I_{1c}$$
$$= \frac{1}{6}E_s tw^3$$

$$S^{in-plane} \cong 2E_s I_y \quad \text{Eq. (11)}$$
$$= 2E_s(twr^2 + I_{2c})$$
$$= 2E_s\left(twr^2 + \frac{1}{12}wt^3\right)$$

From Eq. (10) and (11), it will be appreciated that if the element distance from the reinforced plane 110 (namely r) is significantly less than $0.28\sqrt{w^2-t^2}$, the out-of-plane bending stiffness of the deflectable segment can be still effectively enhanced by so-disposed reinforcing elements as illustrated in FIG. 7D.

From a series of embodiments as illustrated in FIG. 7B, 7C and 7D, it can be appreciated that an anisotropic stiffening element 80 can be incorporated in a deflectable segment 24 in multiple ways. Considering anisotropy of in-plane and out-of-plane bending stiffness as required by controlling planarity of deflection and manufacturability, one incorporating way may be more advantageous than other ways with the cross-sectional selections of both a stiffening element 80 and its placement in a deflectable segment 24. However, it is appreciated from the embodiments that uses of stiffening elements 80 in alternative ways are still within the spirit and scope of this invention.

Figure 6A:
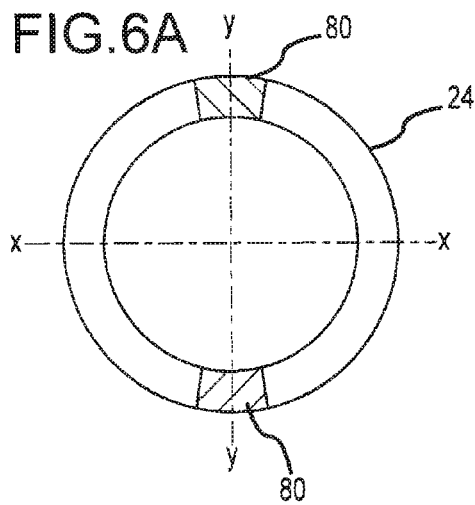
Figure 6B:
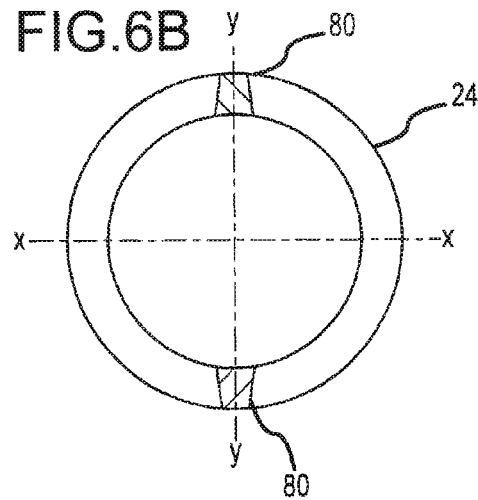
Figure 6C:
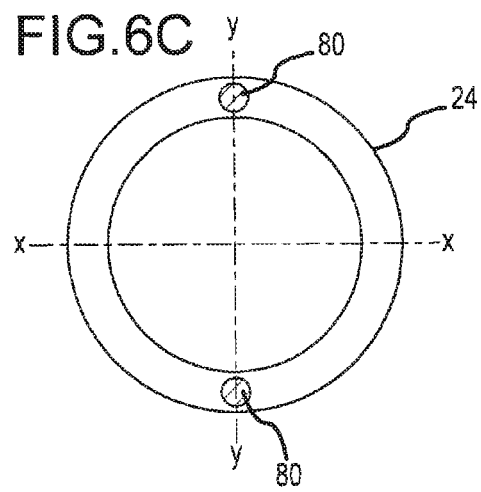
Figure 6D:
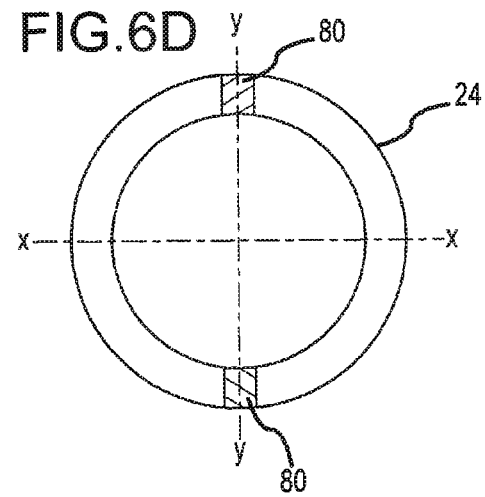
Figure 6E:
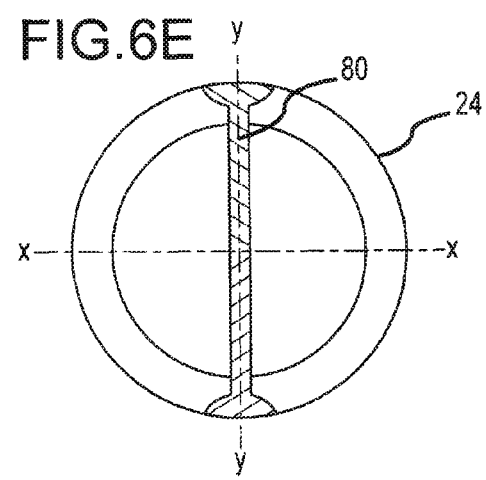
Figure 6F:
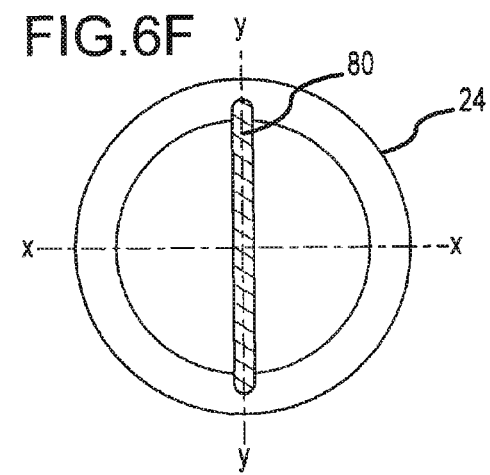

It will be further noted that despite a cross-sectional shape, inclusion of any stiffening element 80 having a Young's modulus (Es) that is greater than the Young's modulus of a material(E) forming the body of the distal deflectable segment 24 will more or less increase out-of-plane bending stiffness of the segment 24, if the element 80 is properly disposed in the segment 24 For instance, referring to FIG. 6C, it is noted that the inclusion of the generally circular metallic or rigid polymer wire/rod-like stiffening elements 80 along the reinforced plane 110 may increases the out-of-plane bending stiffness about the neutral out-of-plane bending axis (i.e., x axis) without significantly changing the in-plane bending stiffness about the neutral in-plane bending axis (i.e., y axis). Further, as shown in FIGS. 6E, 6F and 6J, it will be noted that a single stiffening element may be included along the reinforced plane and may extend entirely across the distal deflectable segment and thereby divide the internal lumen of the deflectable segment into two. As discussed above, such a single stiffening element having the width that is considerably larger than its thickness, when properly disposed in the cross section of a deflectable segment, may significantly increase the out-of-plane bending stiffness of the segment.

Figure 8A:
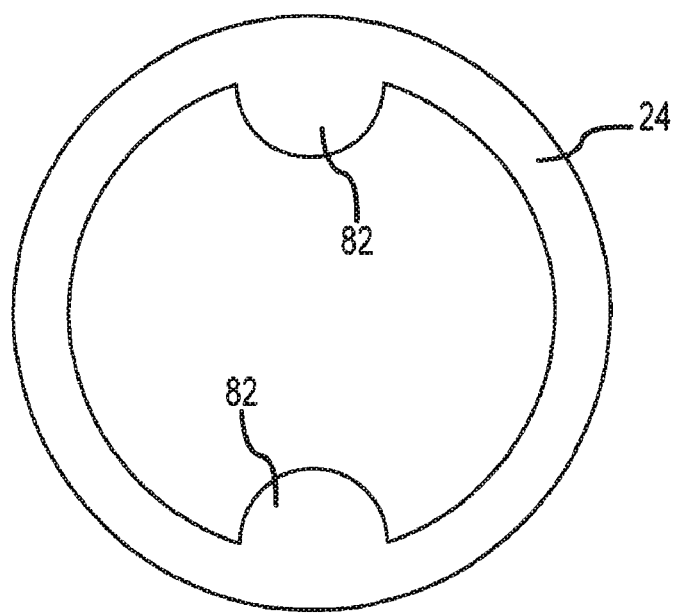
FIGS. 8A and 8B illustrate embodiments of a distal deflectable segment with integral stiffeners.
Figure 8B:
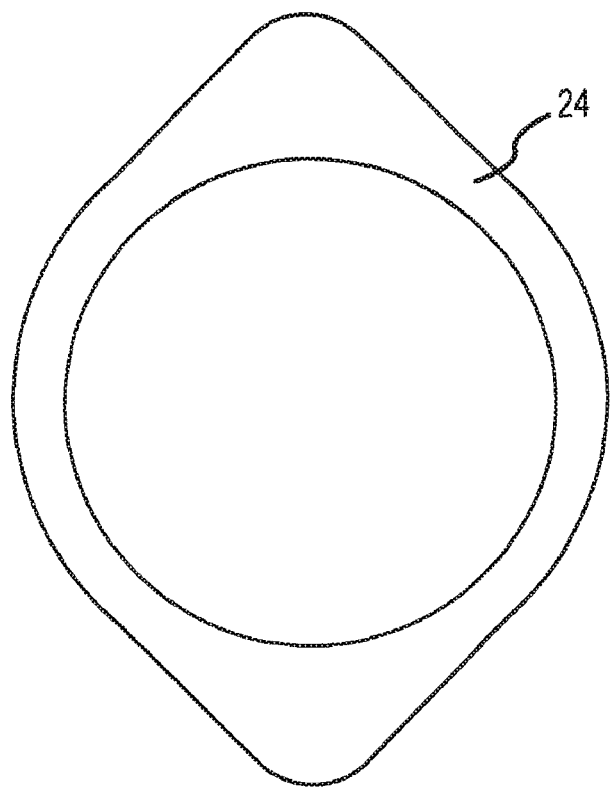

In a further arrangement, the cross section of a distal deflectable segment 24 may be designed or properly shaped to moderately enhance the out-of-plane bending stiffness without utilizing different material and/or separate stiffening elements. FIGS. 8A and 8B illustrate two embodiments where the sidewall thickness and/or shape of the cross-section of the distal deflectable segment 24 are altered to enhance out-of-plane bending stiffness. As shown in FIG. 8A, the distal deflectable segment 24 maintains a generally circular outside surface. However, the sidewall thickness of the distal deflectable segment is non-uniform. More particularly, first and second nodules 82 are formed on the sidewall where the nodules 82 are axially along the deflectable segment 24 and distributed in the vicinity of the reinforced plane 110. As will be appreciated, this non-circular cross section of the segment 24 will increase the area moment of inertia ($I_x$) about the neutral out-of-plane bending axis (i.e. x axis), thereby increasing the out-of-plane bending stiffness of the deflectable segment 24. FIG. 8B illustrates a second embodiment wherein the outside surface of the distal deflectable segment is ovular. Again, area moment of inertia ($I_x$) about the neutral out-of-plane bending axis (i.e. x-axis) will be larger than the area moment of inertia ($I_y$) about the neutral in-plane bending axis (i.e. y-axis) of the distal deflectable segment 24. This will likewise provide anisotropic bending characteristics to the distal deflectable segment.

Although multiple embodiments of this invention have been described above with a certain degree of particularity, those skilled in the art could make numerous alterations to the disclosed embodiments without departing from the spirit or scope of this invention. For example, different cross-sectional shapes of the deflectable segment by increasing or decreasing the sidewall thickness of the deflectable segment 24 and/or various stiffening elements with different combinations of material selections and geometrical shapes as well as their placements in the cross section of, and longitudinally along, a deflectable segment 24 are possible. An important feature of this invention is that the resulting deflectable segment, regardless of the exact configuration of the segment, exhibits anisotropic bending stiffness. Further, it is noted that all directional references (e.g., upper, lower, upward, downward, left, right, leftward, rightward, top, bottom, above, below, vertical, horizontal, clockwise, and counterclockwise) and planar references (e.g. in-plane, out-of-plane, reinforced plane, sweeping plane and the like) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A catheter, comprising:
   a catheter body having a proximal portion and a distal portion said distal portion including a peripheral side wall;
   a selectively deflectable segment in the distal portion, wherein said deflectable segment is substantially tubular having a central lumen, wherein the deflectable segment has side wall stiffening structure at least partially embedded in said peripheral side wall of said distal portion, said selectively deflectable segment having a first bending stiffness for deflection in a first plane and a second bending stiffness for deflection in a second plane and wherein the first bending stiffness and the second bending stiffness are different;
   a tip electrode, disposed at a distal end of said catheter body; and
   deflection actuating structure including:
   an annular ring disposed between the distal portion of said deflectable segment and said tip electrode, wherein an aperture of said annular ring is aligned with said central lumen of said selectively deflectable segment; and
   first and second pull wires extending from said proximal portion and being interconnected to said annular ring, wherein said first and second pull wires are disposed substantially in-plane with one of said first and second planes so as to allow a user to selectively deflect said deflectable segment substantially in the other one of said first and second planes.

2. The catheter of claim 1, wherein the tip electrode further comprises:
   an internal lumen, wherein the internal lumen of the tip electrode is aligned with and in fluid communication with the central lumen of the deflectable segment.

3. The catheter of claim 2, wherein said internal lumen extends through a distal end of said tip electrode.

4. The catheter of claim 1, wherein the first and second planes are substantially aligned with a reference, longitudinal axis of the deflectable segment defined between proximal and distal ends of the deflectable segment when the selectively deflectable segment is in a non-deflected state.

5. The catheter of claim 4, wherein the first and second planes are transverse.

6. The catheter of claim 1, wherein the first bending stiffness is less than the second bending stiffness and the first plane defines a sweeping plane and the second plane defines a reinforced plane.

7. The catheter of claim 6, further comprising:
   a stiffening element disposed along at least a portion of a length of the deflectable segment.

8. The catheter of claim 7, wherein the stiffening element is substantially aligned with the reinforced plane when the deflectable segment is in a non-deflected state.

9. The catheter of claim 1, wherein the stiffening element is disposed proximate to the reinforced plane when the deflectable segment is in a non-deflected state.

10. The catheter of claim 1, wherein at least two stiffening elements are disposed in symmetry with the reinforced plane when the deflectable segment is in a non-deflected state.

11. The catheter of claim 7, wherein the cross section of the stiffening element has a first area moment of inertia $I_{1c}$ about a first centroidal axis that is one or more times greater than a second area moment of inertia $I_{2c}$ about a second centroidal axis of the stiffening element.

12. The catheter of claim 7, wherein the stiffening element is made of a material having a Young's modulus that is greater than the Young's modulus of the body material forming the deflectable segment.

13. The catheter of claim 12, wherein the stiffening element comprises a metallic element.

14. The catheter of claim 12, wherein the body material forming the deflectable segment comprises a polymeric material.

15. The catheter of claim 6, further comprising:
first and second stiffening elements, wherein said first and second stiffening elements are disposed on opposite sides of the sweeping plane.

16. The catheter of claim 1, wherein the second bending stiffness is at least 5% greater than the first bending stiffness.

17. The catheter of claim 1, wherein the second bending stiffness is at least twice the stiffness of the first stiffness.

18. The catheter of claim 1, wherein the second bending stiffness is at least ten times greater than the first bending stiffness.

19. The catheter of claim 1, wherein, in a non-deflected state, the deflectable segment has a substantially circular cross-section.

20. The catheter of claim 1, wherein the deflectable segment is tubular having a substantially circular outside cross-section and a non-uniform wall thickness.

21. The catheter of claim 1, wherein the deflectable segment comprises a first cross dimension and a second cross dimension, wherein a cross dimensions maybe measured along a respective centroidal axis of the cross section of said segment, and wherein the first and second cross dimensions are different.

22. A catheter having a proximal portion and a distal potion, comprising:
a distal deflectable segment having a peripheral side wall, wherein in a non-deflected state a length of the deflectable segment defines a reference longitudinal axis between its proximal and distal ends, wherein the deflectable segment is substantially tubular having a sidewall and a central lumen;
at least one side wall stiffening element at least partially embedded in said peripheral side wall and extending over a portion of the deflectable segment between its proximal and distal ends, wherein the stiffening element is incorporated within the sidewall of the tubular deflectable segment;
at least one pull wire interconnected to the deflectable segment in defined spatial relationship to the side wall stiffening element for selectively deflecting the deflectable segment from the non-deflected state to a deflected state and;
a tip electrode including an internal lumen, wherein said tip electrode is disposed at a distal end of said deflectable element and wherein the internal lumen of the tip electrode is aligned with and in communication with the central lumen of the deflectable segment.

23. The catheter of claim 22, wherein said internal lumen extends through a distal end of said tip electrode.

24. The catheter of claim 22, wherein the distal deflectable segment is formed of a first material and the stiffening element is formed of a second material.

25. The catheter of claim 24, wherein a Young's modulus of the second material is greater than a Young's modulus of the first material.

26. The catheter of claim 24, wherein the first material comprises a polymeric material and the second material comprises a metallic material.

27. The catheter of claim 24, wherein the first material is melt extruded over the second material.

28. The catheter of claim 24, wherein the first material is heat laminated with the second material.

29. The catheter of claim 22, wherein the stiffening element is substantially parallel to the reference longitudinal axis when the deflectable segment is in the non-deflected state, wherein the stiffening element and the reference longitudinal axis define a reinforced plane.

30. The catheter of claim 29, wherein the pull wire is spaced from the reinforced plane.

31. The catheter of claim 30, wherein the pull wire is disposed on an opposite side of the reinforced plane from a second pull wire.

32. The catheter of claim 22,
wherein the tip electrode is guided for in-plane movement to a desired location for treatment of a patient via cooperation of said at least one pull wire and said at least one side wall stiffening element.

33. A guidable catheter having a catheter body with a proximal portion and a distal potion, the distal portion being adapted for insertion into a body, comprising:
a distal deflectable segment formed of a first material, wherein in a non-deflected state the deflectable segment is substantially tubular and a length of the deflectable segment defines a reference axis;
first and second stiffening elements formed of a second material, wherein the stiffening elements are disposed at opposing locations within a sidewall of the deflectable segment, wherein the first and second stiffening elements are disposed in a first plane and wherein the first and second stiffening elements each extend over at least a portion of the length of the deflectable segment;
at least one pull wire interconnected to the deflectable segment, wherein the at least one pull wire is disposed in a second plane that is transverse to the first plane for selectively moving the deflectable segment in-plane from the non-deflected state to a deflected state
a tip electrode, wherein said tip electrode is disposed at a distal end of said deflectable segment in communication with a central lumen of the deflectable segment.

34. The catheter of claim 33, wherein the tip electrode further comprises:
an internal lumen, wherein the internal lumen of the tip electrode is aligned with and in fluid communication with the central lumen of the deflectable segment.

35. A guidable catheter having a catheter body with a proximal portion and a distal potion, the distal portion being adapted for insertion into a body, comprising:
a distal deflectable segment, wherein in a non-deflected state the deflectable segment is substantially tubular having a central lumen and defines a reference, longitudinal axis along its length;
at least one side wall stiffening element extending over at least a portion of a length of the deflectable segment and being at least partially embedded in a peripheral side wall of said distal deflectable element, wherein the stiffening element has an area moment of inertia ($I_{1c}$) about a first centroidal axis perpendicular to said reference axis greater than an area moment of inertia ($I_{2c}$) of a second centroidal axis that is perpendicular to said reference axis;
at least one pull wire interconnected to the deflectable segment in defined spatial relationship to the side wall stiffening element for selectively moving the delectable segment form the non-deflected state to a deflected state; and
a tip electrode, disposed at a distal end of said distal deflectable element and in direct communication with the central lumen, that is guided for in-plane movement to a desired location for treatment of a patient via cooperation of said at least one pull wire and said at least one side wall stiffening element.

36. The catheter of claim 35, wherein said first centroidal axis of the cross section of a deflectable segment, along with said reference, longitudinal axis of the segment, defines a reinforced plane, and said second centroidal axis of the cross section of the segment, along with said reference, longitudinal axis of the segment, defines a sweeping plane.

* * * * *